United States Patent [19]
Sanada et al.

[11] Patent Number: 5,942,186
[45] Date of Patent: Aug. 24, 1999

[54] ADHESIVE PLATE WITH INDICATOR FUNCTION AND INDICATOR THEREFOR

[76] Inventors: Hiromi Sanada, Ho 110, Iwade-machi, Kanazawa-shi, Isikawa; Satoru Numata, 6-14-7 Higashi-Mukojima, Sumida-ku, Tokyo; Kouji Usukura, 571 Mashito, Kasukabe-shi, Saitama; Takayuki Sekine, 3-2-1203 Shibazono-cho, Kawaguchi-shi, Saitama, all of Japan

[21] Appl. No.: 08/770,666

[22] Filed: Dec. 20, 1996

[30] Foreign Application Priority Data

Dec. 22, 1995 [JP] Japan ................................. 7-350189
Feb. 7, 1996 [JP] Japan ................................. 8-045476

[51] Int. Cl.$^6$ ............................................. G01N 33/487
[52] U.S. Cl. ............................ 422/57; 422/61; 436/63; 252/964; 604/332
[58] Field of Search ........................... 422/56–58, 61; 436/63; 73/52, 40; 252/964; 604/332

[56] References Cited

U.S. PATENT DOCUMENTS 3,672,351 6/1972 Ubersax et al. ......................... 422/56
3,675,654 7/1972 Baker et al. ........................... 128/287
3,731,685 5/1973 Eidus ................................... 128/284

*Primary Examiner*—Lyle A. Alexander
*Attorney, Agent, or Firm*—Haverstock, Garrett & Roberts

[57] ABSTRACT

An adhesive plate with an indicator function, and an indicator therefor, according to one embodiment the adhesive plate being comprised of a hydrophilic composition containing a water-soluble coloring matter such as a food color, a dye, a pigment, or metallic salt applied onto or embedded in a part or the whole of a peripheral region of the plate spaced apart from the center thereof, the water-soluble coloring matter being dissolvable in liquid excrements or exudates so as to change color and provide visible indication of the end of the usable life of the adhesive plate. According to another embodiment, the adhesive plate can comprise a hydrophilic composition containing a color development agent applied onto or embedded in a part or the whole of a peripheral region of the plate spaced apart from the center, which, upon contact with liquid excrements or exudates, the hydrophilic composition containing the color development agent is dissolved therein and dropped into a receiving bag attached to the adhesive layer, to permit the color development agent to come into contact with, and react with a coloring reagent previously added to the bag, whereby the color of the color development agent and/or the coloring reagent is changed thereby indicating the limit of the useful life of the adhesive plate.

11 Claims, 3 Drawing Sheets

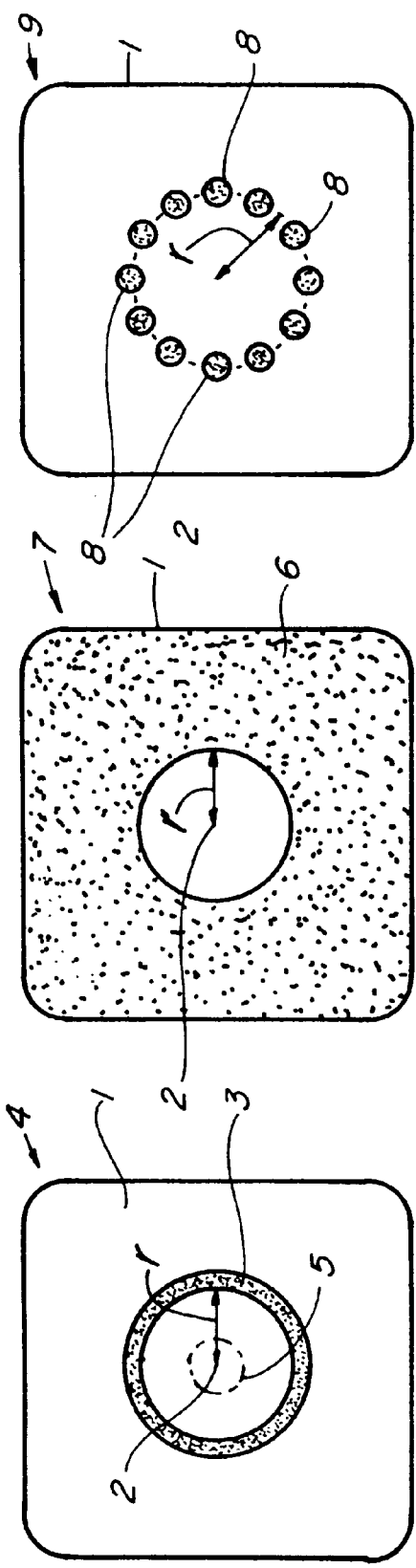

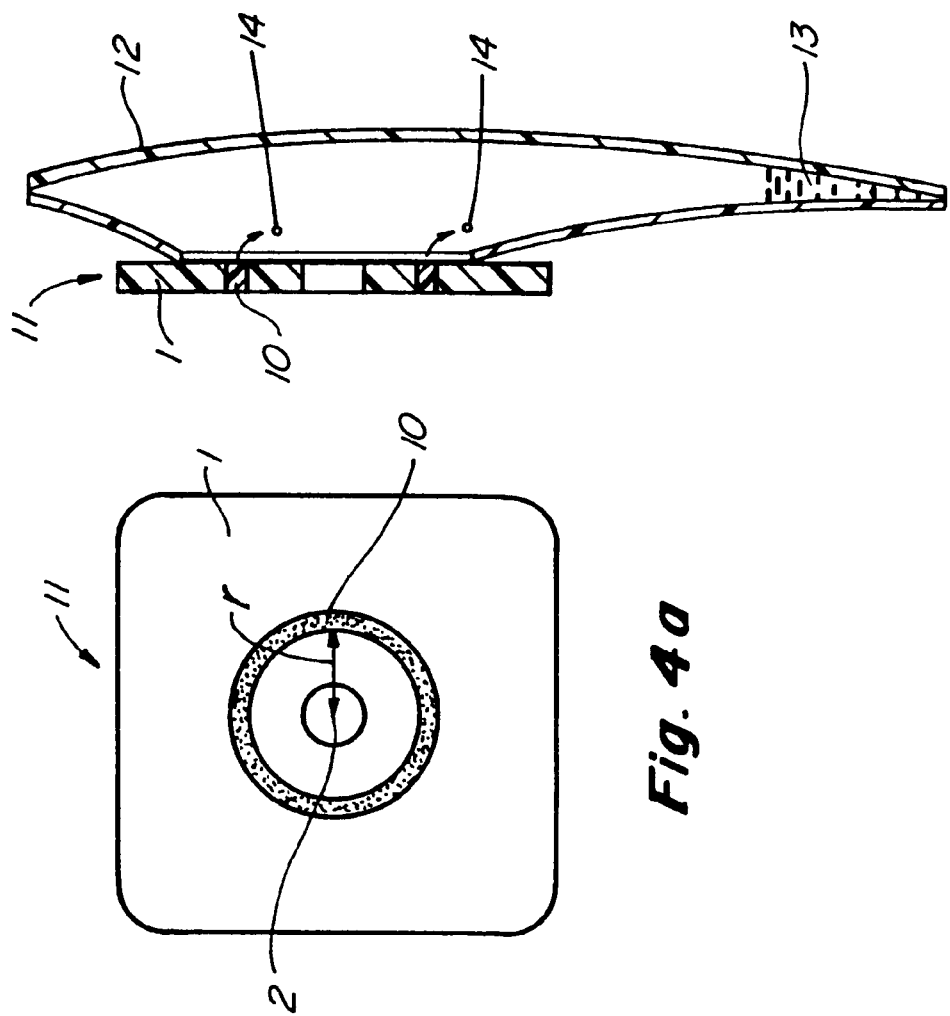

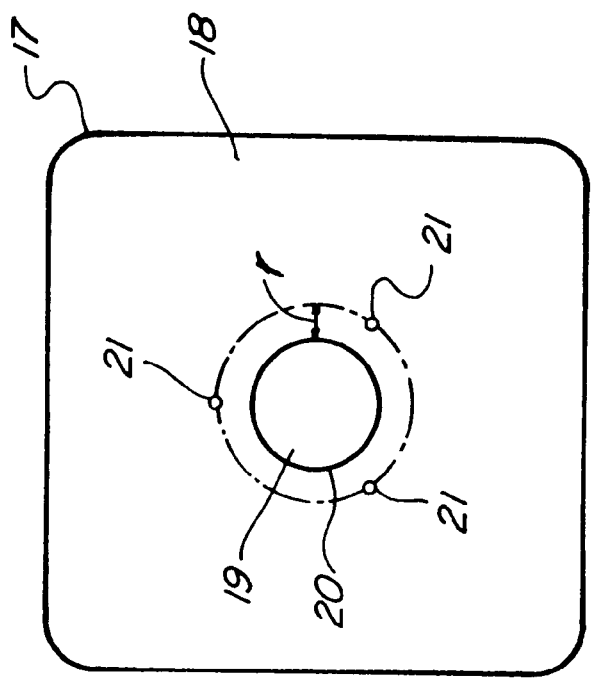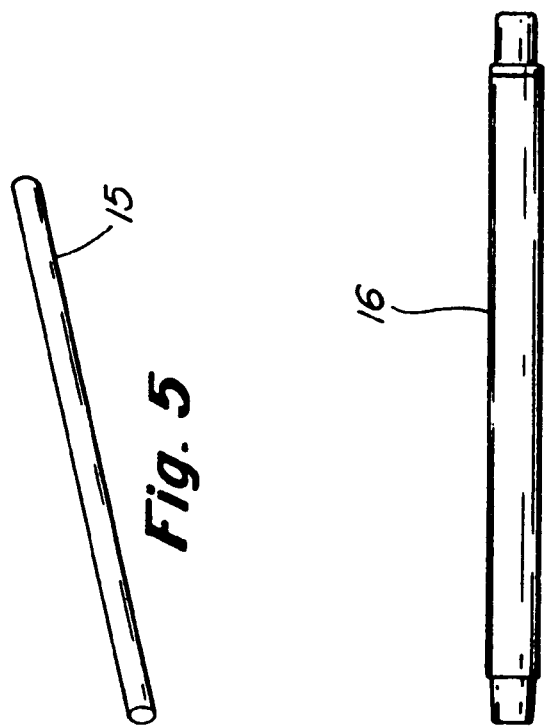

ADHESIVE PLATE WITH INDICATOR FUNCTION AND INDICATOR THEREFOR

The present invention relates to an adhesive plate for use in contact with excrements from a patient with an urostomy or a person with incontinence, and for use in contact with exudates from a patient with a bronchial fistel, as well as to an indicator for visually indicating the end of duration of the effective or useful life of such an adhesive plate.

PRIOR ART

For dealing with excrements from a patient with an urostomy or with incontinence or dealing with liquid exudates from a patient having undergone an operas, use is made of, e.g., an adhesive plate with an adhesive layer around a stoma formed on to surface of the patient's body and a bag attached to the plate for receiving excrements or exudates discharged from the patient's body through the stoma. This adhesive plate is fixed using the adhesive layer onto the patient's skin, thus sealing an area around the stoma. However, a drop with time in the adhesive plate's adhesiveness, caused by perspiration, destroyed horny substance motion of the skin, loading of the receiving bag with excrements etc. from the stoma, can result in problems such as the removal of detachment of the plate from the skin and the leakage of excrements and exudates from between the adhesive plate and the skin.

To solve these problems, there are two known major approaches: one approach is to improve a composition for use in the adhesive layer to strengthen its adhesiveness, for example by adopting a higher compounding ratio of ingredients including elastomers, tackifiers etc. to rubber, acryl, vinyl acetate, silicone, and urethane based adhesive or by varying ingredients including elastomers, tackifiers, fillers etc. The second approach is to improve the durability of the adhesive plate by making improvements in its structure, for example, by enlarging the adhesive area or conferring flexibility and stretchability to the plate. Certainly, the improvement in the composition of the adhesive layer brings about a resultant improvement in durability, but upon removal of the plate, the adhesive layer has been found to cause significant irritation to the skin and deterioration of the horny substances of the skin, so that dermatitis may result. The approach of enlarging the adhesive area has been found to attain no significant improvement in the durability of the adhesive plate because the available space is limited. The approach of conferring flexibility and stretchability on the adhesive plate improves feeling in use, but due to poor adhesiveness and durability, it remains necessary to improve the adhesive strength of the adhesive composition by varying its ingredients, and the resulting adhesive layer with strong adhesivesness causes the above-described problem, as well. Hence, none of the known approaches have achieved an ideal adhesive plate.

A particularly important observation is as follows: at an initial stage for disposing of excrements from a patient with an urostomy or incontinence, or liquid exudates from a patient having undergone an operation, the durability of the adhesive plate must be sufficient to support the attached weight of an ostomy appliance or other device fixed around a resultant stoma or fistula. At this stage on the other hand, the irritation of the adhesive plate on the skin must be indispensably low. These requirements cannot be met by the aforesaid methods. Another requirement is to avoid leakage of excrements because the skin around a stoma is less resistant to such excrements.

Because those who use the adhesive plate have no means of judging the end of its durability under these circumstances, they should exchange the adhesive plate for a new one at an early stage to prevent unexpectable problems. This results in the disposal of a usable plate or in the frequent exchange of a plate, thus causing damages on the skin, while they are forced to live with anxiety for a leakage of excrements.

OBJECTS AND SUMMARY OF THE INVENTION

An object of the present invention is to provide an adhesive plate permitting the visual check of the end of its usability as a result of the deterioration of durability.

Another object of the present invention is to provide an indicator allowing individual marks to accurately indicate the end of usability of an adhesive plate as a result of the deterioration of durability.

To achieve the objects, the adhesive plate of the present invention comprises a hydrophilic composition containing a water-soluble coloring matter applied onto or embedded in a part or a whole of a peripheral region (i.e. apart from the center) of an adhesive layer constituting an adhesive plate body.

Further, the adhesive plate of the present invention comprises a hydrophilic composition containing a water-soluble color development agent applied onto or embedded in a part or the whole of a peripheral region (i.e. apart from the center) of an adhesive layer constituting an adhesive plate body, in combination with an coloring reagent provided in an excrement receiving bag attached to the adhesive layer, the coloring reagent causing chemical reaction upon contact with the color development.

The indicator of the present invention compresses a water-soluble coloring matter solidified with a binder.

FORMS OF EXECUTING THE INVENTION

The adhesive plate of the present invention comprises a hydrophilic composition containing a water-soluble coloring matter such as food colors, dyes, pigments or metallic salts applied onto or embedded in a part or the whole of a peripheral region, and apart from the center, of an adhesive layer constituting an adhesive plate body, so that when liquid excrements or exudates come into contact with the hydrophilic composition, the water-soluble coloring matter is dissolved therein and spread to cause a change in color of the spread coloring matter. By this change, the end of its usability or durability can be checked visually.

Further, the adhesive plate of the present invention comprises a hydrophilic composition containing a color development agent such as an indicator applied onto or embedded in a part or the whole of a peripheral region, and apart from the center, of an adhesive layer constituting an adhesive plate body, so that upon contact with liquid excrements or exudates, the hydrophilic composition containing the color development agent is dissolved therein and dropped from the adhesive layer into a receiving bag attached to the adhesive layer, to permit the color development agent to come into contact with, and react with, a coloring reagent previously added to the bag, whereby the color(s) of the color development agent and/or the coloring reagent is changed. By this discoloration, the limit of its usability or durability can be checked visually.

The adhesive layer may be a conventional one with an example including a mixture of hydrophobic polymers and hydrophilic polymers. Examples of hydrophobic polymers are polyisobutylene, butyl rubber, etc. Examples of hydrophilic polymers are karaya gum, sodium carboxymethylcellulose, pectin, gelatin, etc.

The hydrophilic composition to which the coloring matter or color development agent is added is preferably a mixture of hydrophobic polymers or hydrophobic synthetic resin and hydrophilic polymers. Examples of hydrophobic polymers are polyisobutylene, polybutene, styrene-isoprene-styrene block copolymer, liquid isoprene rubber, isoprene rubber, butyl rubber, liquid rubber, etc. Examples of hydrophobic synthetic resin are epoxy resin, water-soluble hardened urethane resin, polyvinyl pyrrolidone etc. Examples of hydrophilic polymers are karaya gum, sodium carboxymethylcellulose, pectin, guar gum, psyllium seed gum, etc. These may be used singly or in combination.

The water-soluble coloring matter includes the above-mentioned food colors, dyes, pigments and metallic salts. Examples of metallic salts are copper sulfate, cobalt chloride, ferrous sulfate, nickel chloride, etc. The indicator used as the color development agent includes alkaline indicators such as phenolphthalein, phenol red, etc., and acid indicators such as bromocresol green, bromocresol blue, bromocresol purple, bromothymol blue, etc.

The coloring reagent is selected suitably depending on the color development agent used. Examples are dilute sodium hydroxide, dilute potassium hydroxide, water with a high concentration of OH ions, acetic acid, dilute hydrochloric acid, etc.

The indicator of the present invention is prepared from a food color as the water-soluble coloring matter, and is formed advantageously into a thin rod by use of wax as a binder to solidify the food color. This rod shaped indicator is broken and the resulting fragment is embedded by hand into a predetermined position apart from the center of the adhesive layer of the adhesive plate. When liquid excrements or exudates, discharged from the opening of the adhesive plate, permeate to come into contact with the embedded indicator, the coloring agent is dissolved therein and spread to change the color of the adhesive layer on that region. By this change, the end of its usability or durability can be known visually. The end of its usability or durability can also be known visually when the coloring matter is dissolved in excrements and dropped as a colored fragment from the adhesive layer into the excrement receiving bag attached to the adhesive plate.

The binder may be any water-soluble or hydrophobic binder insofar as it is capable of solidifying the coloring matter, is solid at a certain temperature (40° C. or less) slightly higher than body temperature, and is safe for the human body. As the wax, use can be made of carnauba wax, paraffin wax or micro wax or a mixture thereof, preferably carnauba wax for coloration, breakage, hardness, and dimension accuracy. It is also possible to use epoxy resin-based adhesives, hot-melt resin, polyvinyl pyrrolidone, monoalkyl esters of poly(methyl vinyl ether/maleate), etc. although they are slightly inferior in practical use with respect to breakage and dimensional accuracy.

In the case of solidifying the coloring matter with the binder, it is preferred for convenience of operation that the resulting solidified coloring agent is pencil-lead-shaped and introduced into an applicator having the same delivery mechanism as in a mechanical pencil, by which the rod-shaped coloring agent can be pushed out of the top of the applicator, then forced into the adhesive layer of the adhesive plate, and broken in a suitable length. Alternatively, the coloring matter is formed into particles and each particle is embedded in the adhesive layer. Unlike the rod-shaped coloring agent this particle coloring matter is not required to be broken.

BRIEF DESCRIPTION OF THE DRAWINGS

FIG. 1 is a front view of one embodiment of an adhesive plate according to the present invention;

FIG. 2 is a front view of another embodiment of an adhesive plate according to the present invention;

FIG. 3 is a front view of another embodiment of an adhesive plate according to the present invention;

FIG. 4a and FIG. 4b are a front view and a longitudinal side view of another embodiment of an adhesive plate according to the present invention, respectively;

FIG. 5 is a perspective view of one embodiment of an indicator according to the present invention;

FIG. 6 is a front view of one embodiment of an applicator for use with the indicator of FIG. 5; and FIG. 7 is a front view of the indicator of the present invention used in a typical adhesive plate.

DETAILED DESCRIPTION OF THE PREFERRED EMBODIMENTS

First, the adhesive plate of the present invention is illustrated by reference to the following examples.

The adhesive layer used as the main body of the adhesive plate in the following examples was prepared by mixing of about 80 parts by weight of polyisobutylene, about 20 parts by weight of butyl rubber, about 30 parts by weight of karaya gum, about 30 parts by weight of carboxymethylcellulose, and about 30 parts by weight of pectin and then forming the mixture into a square-shaped plate.

EXAMPLE 1

About 20 to about 90% by weight of liquid isoprene rubber as the hydrophobic polymer were mixed with about 80 to about 10% by weight of pection as the hydrophilic polymer containing a dye as the water-soluble coloring matter. As shown in FIG. 1, the resulting hydrophilic composition 3 containing the dye was embedded in a ring shape into a position apart by the predetermined distance "r" from the center 2 of the adhesive layer 1 prepared as described above. The adhesive plate 4 is provided in the center with an opening as shown in broken line 5 the size of which depends on a user's stoma and this opening is fixed around the stoma. When liquid excrements from the stoma has permeated into the composition 3 due to the deterioration or partial removal of the adhesive layer, the dye in the composition 3 is dissolved in the excrements to be spread into the adhesive layer, thus causing a change in color on that region. The user can know the time for exchange of the adhesive plate by visually checking this color change.

EXAMPLE 2

About 20 to about 90% by weight of polyisobutylene as the hydrophobic polymer was mixed with 80 about to about 10% by weight of karaya gum and pectin as the hydrophilic polymers containing a food color as the water-soluble coloring agent. As shown in FIG. 2, the resulting hydrophilic composition 6 containing the water-soluble coloring matter was applied onto the whole surface ranging from a position apart by predetermined distance "r" from the center 2 of the adhesive layer 1 to the periphery of the adhesive layer. When liquid excrement has permeated into the composition 6, the food color in the composition is dissolved in the excrements to be spread into the adhesive layer, thus causing a change in color on that region.

EXAMPLE 3

About 20 to about 90% by weight of butyl rubber as the hydrophobic polymer was mixed with about 80 to about 10% by weight of guar gum as the hydrophilic polymer containing a metallic salt cobalt chloride as the water-soluble coloring matter. As shown in FIG. 3, the resulting hydrophilic composition 8 containing the water-soluble coloring matter was embedded intermittently in a circle form having the predetermined radius "r" apart from the center 2 of the adhesive layer 1. When liquid excrements has permeated into the composition 8, the metallic salt in the composition 8 is dissolved in the exocrine method of making a paste of the hydrophilic composition involves mixing of about 90 to about 30% by weight of liquid rubber (liquid isoprene rubber such as Claprene L-IR-50, L-IR-30 and L-IR-503 by Kuraray Co., Ltd. and liquid polybutene such as Nisseki polybutene HV-1900 etc.), 10 to 70% by weight of the above-mentioned hydrophilic substance (e.g. natural polysaccharides and synthesized products, including karaya gum, pectin, gum Arabic, carrageenan, dammar gum, gelatin, CMC (Sodium carboxy methyl cellulose), HMC (hydroxy methyl cellulose), etc. hydroxide 13 as the coloring reagent. When liquid excrements has permeated into the composition 10, the composition 10 containing phenolphthalein is dissolved in the liquid excrements to be separated from the adhesive layer 1 and dropped into the receiving bag 12. In this way, when this separated fragment (a component of the color development agent) 14 comes into contact with dilute sodium hydroxide 13, chemical reaction occurs to induce a clear change in the color of the phenolphthalein. The user can know the time for exchange of the adhesive plate by visually checking this color change which can be seen from the outside of the receiving bag.

For each of the above examples, the hydrophilic composition containing the coloring matter or the color development agent may be provided in various manners in addition to the above illustrated manners in the drawings, by permitting the composition to be embedded in or applied onto the adhesive layer in a region apart by a predetermined distance from the center of the adhesive layer.

The hydrophilic compositions containing the water-soluble coloring matter or the color development agent, as illustrated in the above examples, were provided in the adhesive layer at the time of manufacturing, but the composition can also be provided just before use. That is, the hydrophilic composition containing the water-soluble coloring matter or color development agent may be formed into a paste and may, just before use, be applied in a suitable amount onto the adhesive layer of the adhesive plate. One method of making a paste of the hydrophilic composition involves mixing of about 90 to about 30% by weight of liquid rubber (liquid isoprene rubber such as Claprene L-IR-50, L-IR-30 and L-IR-503 by Kuraray Co., Ltd. and liquid polybutene such as Nisseki polybutene HV-1900 etc.), 10 to 70% by weight of the above-mentioned hydrophilic substance (e.g. natural polysaccharides and synthesized products, including karaya gum, pectin, gum Arabic, carrageenan, dammar gum, gelatin, CMC (Sodium carboxy methyl cellulose), HMC (hydroxy methyl cellulose), etc.), and about 0.1 to about 3% by weight of the above-mentioned water-soluble coloring matter or color development agent.

The mixture may additionally contain a suitable amount of elastomer, tackifier, dispersant, solvent, etc. A viscous substance such as poly (methylvinyl ether maleate) monoalkyl ester, polyvinyl pyrrolidone etc. can also be used in place of the liquid rubber. This paste hydrophilic composition, upon application, has been found not to cause a drop in the adhesive strength of the adhesive layer. Because the hydrophilic composition containing the coloring matter or color development agent can be applied just before use, it is possible to prevent the composition from undergoing discoloration with time during storage, which is difficult to distinguish from discoloration occurring upon contact with liquid excrements or exudates.

Next, the indicator of the present invention is illustrated by reference to the following examples.

EXAMPLE 1

About 80 parts by weight of carnauba wax No. 1 manufactured by Noda Wax Corp. a as carnauba wax and about 15 parts by weight of mobile wax 140 manufactured by Mobile Petroleum Co., Ltd. as a paraffin wax as the binder, and about 5 parts by weight of food coloring were mixed and formed into a solid rod of about 1.5 mm in diameter whereby the indicator 15 as shown in FIG. 5 was obtained. For use, this rod was introduced into an applicator 16 having the same delivery mechanism as in a mechanical pencil, as shown in FIG. 6. This indicator was extremely excellent in practical use because it was excellent in color development, and it had suitable hardness and could be sharply broken after forced by the applicator into the adhesive layer of the adhesive plate, and it was further excellent in dimensional accuracy at the time of manufacture.

EXAMPLE 2

About 50 parts by weight of the same carnauba wax as in Example 1 and about 30 parts by weight of the same paraffin wax as in Example 1, about 15 parts by weight of micro wax available under the tradename 190Y as the binder, and about 5 parts by weight of a food color were mixed and formed into a solid rod. It had sufficient practical usability because its color development and dimensional accuracy were excellent similarly to that of Example 1 and its breakage and hardness also were excellent though slightly inferior to that of Example 1.

EXAMPLE 3

About 40 parts by weight of the same carnauba wax as in Example 1, about 40 parts by weight of the same paraffin wax as in Example 1 and about 15 parts by weight of the same micro wax as in Example 2 as the binder, and about 5 parts by weight of a food color were mixed and formed into a solid rod. Its color development and dimensional accuracy were excellent but its hardness was slightly low, and its breakage was problematic. However, its practical usability was still adequate.

EXAMPLE 4

About 45 parts by weight of the same paraffin wax as in Example 1 and about 50 parts by weight of the same micro wax as in Example 2 as the binder, and about 5 parts by weight of a food color binder were mixed and formed into a solid rod. Its color development and dimensional accuracy were excellent but its hardness was slightly low, and its breakage was problematic. However, its practical usability was adequate.

EXAMPLE 5

About 95 parts by weight of a two-component liquid-type adhesive (Konishi Co., Ltd.) as an epoxy resin-based adhesive as the binder and about 5 parts by weight of a food color were mixed and formed into a solid rod. Its color development was excellent, and its hardness and dimensional accuracy were slightly low and its breakage was problematic. However, its practical usability was still adequate.

EXAMPLE 6

About 95 parts by weight of a hot-melt type adhesive (Highsol Co., Ltd.) as the hot-melt resin as the binder and about 5 parts by weight of a food color were mixed and formed into a solid rod. Its color development was excellent, and its hardness and dimensional accuracy were slightly low and its breakage was problematic. However, its practical usability was still adequate.

EXAMPLE 7

About 95 parts by weight of PVPK-90 (ISP Japan K.K.) as polyvinyl pyrrolidone as the binder and about 5 parts by weight of a food color were mixed and formed into a solid rod. Its color development was excellent, and its hardness and dimensional accuracy were slightly low and its breakage was problematic. However, its practical usability was still adequate.

The method of using the above indicator is described below. As shown in FIG. 7, the adhesive plate 17 is provided at its skin-contact side with the adhesive layer 18. Its center is provided with an opening 19, the size of which can be varied depending on the size of a user's stoma. The thin fragment 21 from the indicator (i.e. a broken thin fragment of suitable size in the case of the rod-shaped indicator, or a particle itself in the case of the particle indicator) is embedded in a peripheral region apart by the predetermined distance "r", usually between about 15 and 20 mm, from the periphery 20 of the opening 19.

The adhesive plate thus provided with the indicator is fixed via the adhesive layer to the skin region around a stoma. Generally, the adhesive plate is designed to be usable for 3 to 5 days, but the adhesiveness of the adhesive plate rapidly drops if its fixing is not enough, sweat occurs, or there is much water in excrements, so that the excrements begin to permeate through the adhesive plate. When the excrements reach the position where the indicator was fixed, the water-soluble coloring matter is dissolved therein and dispersed therearound to indicate the end of durability of the adhesive plate. After a certain period, a part of this coloring matter is dropped into the receiving bag attached to the adhesive plate to permit visualization.

According to the present invention, there are achieved the following effects:

An advantage of the adhesive plate of the present invention is that because the permeation of liquid excrements accompanying the deterioration of the adhesive layer is used as the sign of the deterioration of the plate and detected as a change in color of the hydrophilic composition containing the coloring matter or color development agent, the user can reliably know the end of usability of the adhesive plate and can continue using the plate confidently without anxiety for the full life of the sheet. Another advantage is that the occurrence of skin disorders can be reduced because the adhesive plate sheet itself can be constituted such that it has the most suitable adhesiveness on the skin.

An advantage of the indicator of the present invention is that because the indicator can be attached to a predetermined portion depending on the size of a patient's stoma of the adhesive plate, the user can know the accurate end of usability of the adhesive plate in his or her own case, and thus he or she can use the adhesive plate without anxiety for the full life of the sheet. Another advantage is that because the adhesive plate can be marked just before use, it is free of discoloration during storage, as often occurs in an adhesive plate previously marked, so the user can know the accurate end of it usability.

Thus, there has been shown and described several embodiment of an adhesive plate with indicator function and indicator therefor which fulfill all of the objects and advantages set forth above. It will be apparent to those skilled in the art, however, that many changes, modifications, variations and other uses and applications for the subject invention are possible. All such changes, modifications, variations and other uses which do not depart from the spirit and scope of the invention are deemed to be covered by the invention, which is limited only by the claims which follow.

What is claimed is:

1. An adhesive plate with an indicator function, wherein a hydrophilic composition containing a water-soluble coloring matter is provided in a part or the whole of a peripheral region in or on a surface of an adhesive layer constituting an adhesive plate body, the adhesive layer having a center, said peripheral region being at a position apart by a predetermined distance from the center of the adhesive layer, said coloring matter being capable of dissolving in excrements and separating from the adhesive layer as a colored fragment for providing the indicating function.

2. The adhesive plate according to claim 1, wherein the water-soluble coloring matter is selected from the group consisting of food colors, dyes, pigments and metallic salts.

3. An adhesive plate with an indicator function, comprising a hydrophilic composition containing a color development agent provided in a part or the whole of a peripheral region in or on a surface of an adhesive layer constituting an adhesive plate body, the adhesive layer having a center, said peripheral region being spaced apart by a predetermined distance from the center of the adhesive layer, and a coloring reagent provided in an excrement-receiving bag attached to the adhesive layer, said color development agent being capable of dissolving in excrements and separating from the adhesive layer for providing the indicating function by means of a chemical reaction upon contact with said coloring agent.

4. The adhesive plate according to claim 3, wherein the color development agent is an indicator.

5. An indicator for an adhesive plate, said indicator comprising a water-soluble coloring matter solidified with a binder and wherein the solidified coloring matter is embedded in a part or the whole of a peripheral region in an adhesive layer constituting an adhesive plate body of the adhesive plate, solidified coloring matter being capable of dissolving in liquid excrement or exudates and providing an indicating function by spreading to change the color of the region or separating from the adhesive layer as a colored fragment.

6. The indicator according to claim 5 wherein the water-soluble coloring matter is a food color.

7. The indicator according to claim 5, wherein the binder is a wax, said wax being capable of solidification of the water-soluble coloring matter.

8. The indicator according to claim 5, wherein the water soluble coloring matter is solidified into a thin rod with the binder and thin fragments from said rod are embedded in the part or the whole of the peripheral region in the adhesive layer constituting the adhesive plate body.

9. The indicator according to claim 5, wherein the water-soluble coloring matter is solidified into particles with the binder.

10. A method of using the indicator according to claim 5, which comprises marking the surface of an adhesive layer constituting an adhesive plate, by means of a thin fragment of the indicator embedded in a predetermined position in a peripheral region apart from the center of the adhesive layer.

11. The adhesive plate according to claim 1, wherein the center of the adhesive layer comprises an opening extending through the adhesive plate body adapted for the passage of excrements therethrough.

\* \* \* \* \*

UNITED STATES PATENT AND TRADEMARK OFFICE
CERTIFICATE OF CORRECTION

PATENT NO. : 5,942,186

DATED : August 24, 1999

INVENTOR(S) :

Hiromi Sanada

It is certified that error appears in the above-identified patent and that said Letters Patent is hereby corrected as shown below:

Col. 1, line 14, "operas" should be --operation--.

Col. 1, line 17, "to" should be --the--.

Signed and Sealed this

Fourth Day of January, 2000

Attest:

*Attesting Officer*     *Acting Commissioner of Patents and Trademarks*